United States Patent [19]
Dhalla et al.

[11] Patent Number: 6,043,259
[45] Date of Patent: Mar. 28, 2000

[54] TREATMENT OF CARDIOVASCULAR AND RELATED PATHOLOGIES

[75] Inventors: Naranjan S. Dhalla; Rajat Sethi; Krishnamurti Dakshinamurti, all of Winnipeg, Canada

[73] Assignees: Medicure Inc.; University of Manitoba, both of Winnipeg, Canada

[21] Appl. No.: 09/276,280

[22] Filed: Mar. 25, 1999

Related U.S. Application Data

[63] Continuation-in-part of application No. 09/112,277, Jul. 9, 1998
[60] Provisional application No. 60/052,449, Jul. 14, 1997.
[51] Int. Cl.⁷ .................................................... A01N 43/40
[52] U.S. Cl. ........................... 514/345; 514/351; 514/821
[58] Field of Search ................................... 514/345, 351, 514/821

[56] References Cited

U.S. PATENT DOCUMENTS

| | | |
|---|---|---|
| 3,206,463 | 9/1965 | Baetz . |
| 3,910,921 | 10/1975 | Esanu . |
| 3,987,177 | 10/1976 | Giudicelli et al. . |
| 4,032,534 | 6/1977 | Chodkiewicz . |
| 4,036,844 | 7/1977 | Thorne et al. . |
| 4,053,607 | 10/1977 | Thorne et al. . |
| 4,137,316 | 1/1979 | Esanu . |
| 4,167,562 | 9/1979 | Evers . |
| 4,361,570 | 11/1982 | Fici . |
| 4,369,172 | 1/1983 | Schor et al. . |
| 4,374,841 | 2/1983 | Descamps et al. . |
| 4,515,771 | 5/1985 | Fine . |
| 4,567,179 | 1/1986 | Lombardino . |
| 4,581,363 | 4/1986 | Esanu . |
| 4,605,741 | 8/1986 | Zagnoli et al. . |
| 4,735,950 | 4/1988 | Esanu . |
| 4,735,956 | 4/1988 | Baldwin et al. . |
| 4,837,239 | 6/1989 | Benjamin et al. . |
| 4,843,071 | 6/1989 | Hohenwarter . |
| 4,962,121 | 10/1990 | Hamberger et al. . |
| 5,001,115 | 3/1991 | Sloan . |
| 5,053,396 | 10/1991 | Blass . |
| 5,118,505 | 6/1992 | Költringer . |
| 5,130,324 | 7/1992 | Ulrich et al. . |
| 5,132,115 | 7/1992 | Wolter et al. . |
| 5,210,083 | 5/1993 | Pfirrmann . |
| 5,213,813 | 5/1993 | Kornecki et al. . |
| 5,254,572 | 10/1993 | Serfontein ............................. 514/345 |
| 5,272,165 | 12/1993 | Ulrich et al. . |
| 5,278,154 | 1/1994 | Lacoste et al. . |
| 5,288,716 | 2/1994 | Speck ....................... 514/89 |
| 5,326,757 | 7/1994 | Demopoulos . |
| 5,328,453 | 7/1994 | Sibalis . |
| 5,372,999 | 12/1994 | Schneider et al. . |
| 5,385,937 | 1/1995 | Stamler et al. . |
| 5,420,112 | 5/1995 | Lewis et al. . |
| 5,441,972 | 8/1995 | Ogata et al. . |
| 5,504,090 | 4/1996 | Neely . |
| 5,563,126 | 10/1996 | Allen et al. . |
| 5,569,459 | 10/1996 | Shlyankevich . |
| 5,569,648 | 10/1996 | Lewis et al. . |
| 5,631,271 | 5/1997 | Serfontein . |
| 5,633,228 | 5/1997 | Lewis et al. . |
| 5,648,335 | 7/1997 | Lewis et al. . |
| 5,728,684 | 3/1998 | Cheng et al. . |
| 5,733,884 | 3/1998 | Barbul et al. . |
| 5,733,916 | 3/1998 | Neely . |
| 5,770,215 | 6/1998 | Moshyedi . |
| 5,795,873 | 8/1998 | Allen . |
| 5,804,163 | 9/1998 | Gibby et al. . |
| 5,804,594 | 9/1998 | Murad . |
| 5,833,998 | 11/1998 | Biedermann et al. . |
| 5,834,446 | 11/1999 | Dow et al. . |
| 5,840,685 | 11/1998 | Fujii et al. . |
| 5,847,008 | 12/1998 | Doebber et al. . |
| 5,858,017 | 1/1999 | Demopulos et al. . |
| 5,859,051 | 1/1999 | Adams et al. . |
| 5,874,420 | 2/1999 | Pelleg . |
| 5,874,443 | 2/1999 | Kiely et al. . |
| 5,888,514 | 3/1999 | Weisman . |

FOREIGN PATENT DOCUMENTS

| | | |
|---|---|---|
| 83350 | 1/1976 | Belgium . |
| 863754 | 5/1978 | Belgium . |
| 0 121 036 A1 | 10/1984 | European Pat. Off. . |
| 0 144 051 A2 | 6/1985 | European Pat. Off. . |
| 0 891 719 A1 | 1/1999 | European Pat. Off. . |
| 846376 | 3/1941 | France . |
| 5552 | 12/1967 | France . |
| 5453 | 12/1968 | France . |
| 1579544 | 8/1969 | France . |
| 2101010 | 3/1972 | France . |
| 2255883 | 7/1975 | France . |
| 2428640 | 1/1980 | France . |
| 1 958 226 | 5/1970 | Germany . |
| 24 61 742 | 7/1976 | Germany . |
| 37 05 549 A1 | 9/1988 | Germany . |
| 43 44 751 A1 | 6/1995 | Germany . |
| 48-21959 | 7/1973 | Japan . |
| 54-17130 | 2/1979 | Japan . |
| 561 183 | 4/1975 | Switzerland . |
| 1 013 939 | 12/1965 | United Kingdom . |
| 1 201 014 | 8/1970 | United Kingdom . |
| 1 297 080 | 11/1972 | United Kingdom . |
| 1 360 536 | 7/1974 | United Kingdom . |
| 1 493 993 | 12/1977 | United Kingdom . |
| 2 254 556 | 10/1992 | United Kingdom . |
| WO 83/00085 | 1/1983 | WIPO . |
| WO 91/19500 | 12/1991 | WIPO . |
| WO 94/18965 | 9/1994 | WIPO . |
| WO 99/03365 | 1/1999 | WIPO . |

OTHER PUBLICATIONS

Chemical Abstract 124:193847, "Effect of Oral Pyridoxine Hydrochloride Supplementation on Arterial Blood Pressure in Patients with Essential Hypertension", Dec. 1995.

(List continued on next page.)

*Primary Examiner*—Frederick Krass
*Attorney, Agent, or Firm*—Merchant & Gould P.C.

[57] ABSTRACT

Compositions and methods for treatment and prevention of hypertrophy, hypertension, congestive heart failure, ischemic heart disease, ischemia-related conditions, such as ischemia reperfusion injury and cellular dysfunction, are described. The methods are directed to administering pharmaceutical compositions containing at least one compound selected from pyridoxal-5'-phosphate, pyridoxine, pyridoxal, and pyridoxamine.

25 Claims, No Drawings

OTHER PUBLICATIONS

"B Vitamins May Cut Heart Disease Risk", *Harvard Health Letter*, 1 page (1998).

Barrett, S., "Homocysteine: A Cardiovascular Risk Factor Worth Considering", http://www.quackwatch.com/03HealthPromotion/homocysteine.html, 2 pages (©1997).

Bernstein, A., "Vitamin $B_6$ in Clinical Neurology", *Annals of New York Academy of Sciences*, vol. 585, pp. 250–260 (1990).

Berger, A.R. et al., "Dose response, coasting, and differential fiber vulnerability in human toxic neuropathy: A prospective study of pyridoxine neurotoxicity", *Neurology*, vol. 42, No. 7, pp. 1367–1370 (Jul. 1992).

Bode, W. et al., "Pyridoxal-5'-Phosphate and Pyridoxal Biokinetics in Male Wistar Rats Fed Graded Levels of Vitamin B–6", *J. Nutr.*, vol. 121, No. 11, pp. 1738–1745 (Nov. 1991).

Chasan—Taber, L. et al, "A Prospective Study of Folate and Vitamin $B_6$ and Risk of Myocardial Infarction in US Physians", *Journal of the American College of Nutrition*, vol. 15, No. 2, pp. 136–143 (Apr. 1996).

Cho, Y. et al., "In Vivo Evidence for a Vitamin B–6 Requirement in Carnitine Synthesis", *J. Nutr.*, vol. 120, pp. 258–265 (1990).

"Computer Generated Search Reports", 70 pages (May 1999).

Ellis, J. et al., "Prevention of Myocardial Infarction by Vitamin $B_6$", *Res. Commun. Molec. Pathol. Pharmacol.*, vol. 89, No. 2, pp. 208–220 (Aug. 1995).

Harada, K. et al., "Studies on Vitamin $B_6$, (IV) Behavior of Pyridoxal Acylates in the Body After Parenteral Administration", *Vitamins Journal of the Vitamin Society of Japan*, vol. 45, No. 2, pp. 69–75 (Feb. 1972).

Hoover, D.M. et al., "Ultrastructural Lesions of Pyridoxine Toxicity in Beagle Dogs", *Vet. Pathol.*, vol. 18, pp. 769–777 (1981).

Kok, F. et al., "Low Vitamin $B_6$ Status in Patients with Acute Myocardial Infarction", *Am. J. Cardiol.*, vol. 63, pp. 513–516 (Mar. 1, 1989).

Krinke, G. et al., "Pyridoxine Megavitaminosis: An Analysis of the Early Changes Induced with Massive Doses of Vitamin $B_6$ in Rat Primary Sensory Neurons", *J. Neuropathol. Exp. Neurol.*, vol. 44, No. 7, pp. 117–129 (Mar. 1985).

Lal, K. et al., "Hypotensive action of 5–HT receptor agonists in the vitamin $B_6$—deficient hypertensive rat", *Eur. J. Pharmacol.*, vol. 234, Nos. 2/3, pp. 183–189 (Apr. 1993).

Lal, K. et al., "Calcium channels in vitamin $B_6$ deficiency—induced hypertension", *Journal of Hypertension*, vol. 11, No. 12, pp. 1357–1362 (Dec. 1993).

Lal, K. et al., "The effect of vitamin $B_6$ on the systolic blood pressure of rats in various animal models of hypertension", *Journal of Hypertension*, vol. 14, No. 3, pp. 355–363 (Mar. 1996).

Merrill, Jr. et al. "Diseases associated with defects in vitamin $B_6$ metabolism or utilization", *Ann. Rev. Nutr.*, vol. 7, pp. 137–156 (1987).

Omenn, G. et al., "Preventing Coronary Heart Disease", *Circulation*, vol. 97, pp. 421–424 (1998).

Paulose, C. et al., "Sympathetic Stimulation and Hypertension in the Pyridoxine—Deficient Adult Rat", *Hypertension*, vol. 11, No. 4, pp. 387–391 (Apr. 1988).

Rimm, E. et al., "Folate and Vitamin $B_6$ From Diet and Supplements in Relation to Risk of Coronary Heart Disease Among Women", *JAMA*, vol. 279, No. 5, pp. 359–364 (Feb. 4, 1998).

Trezise, D. et al., "$P_2$ purinoceptor antagonist properties of pyridoxal–5–phosphate", *Eur. J. Pharmacol.*, vol. 259, No. 3, pp. 295–300 (Jul. 11, 1994).

Verhoef, P. et al., "Homocysteine Metabolism and Risk of Myocardial Infarction: Relation with Vitamins $b_6$, $B_{12}$, and Folate", *Am. J. Epidemiol.*, vol. 143, No. 9, pp. 845–859 (May 1, 1996).

Vermaak, W.J.H. et al., "Vitamin $B_6$ and coronary artery disease. Epidemiological Observations and Case studies", *Atherosclerosis*, vol. 63, pp. 235–238 (Feb. 1987).

Windebank, A., "Neurotoxicity of Pyridoxine Analogs Is Related to Coenzyme Structure", *Neurochemical Pathology*, vol. 3, pp. 159–167 (1985).

Zempleni, J. et al., "The utilization of intravenously infused pyridoxine in humans", *Clinica Chimica Acta*, vol. 229, Nos. 1, 2, pp. 27–36, (Sep. 1994).

TREATMENT OF CARDIOVASCULAR AND RELATED PATHOLOGIES

This is a continuation-in-part application of application Ser. No. 09/112,277 of Jul. 9, 1998, which claims the benefit of provisional application Ser. No. 60/052,449 of Jul. 14, 1997.

FIELD OF THE INVENTION

This invention relates to a method of treating hypertrophy, hypertension, congestive heart failure, ischemic heart disease, ischemia reperfusion injuries in various organs and to treating cellular dysfunction including arrhythmia and heart failure subsequent to myocardial infarction.

BACKGROUND

Heart failure is the pathophysiological state in which heart is unable to pump blood at a rate commensurate with the requirement of the metabolizing tissues or can do so only from an elevated filling pressure (increased load). With time when this condition leads to excess fluid accumulation such as peripheral edema it is referred to as congestive heart failure.

When an excessive pressure or volume load is imposed on the ventricle myocardial hypertrophy develops, providing a compensatory mechanism that permits the ventricle to sustain an increased load. However, a ventricle subjected to an abnormally elevated load for a prolonged period may fail to maintain compensation despite the presence of ventricular hypertrophy and pump failure may ultimately occur.

Hypertension is defined as an increase in resistance to blood flow through the vascular system. This resistance leads to increases in systolic and or diastolic blood pressures. Hypertension places increased tension to the left ventricular myocardium, causing it to stiffen and hypertrophy and accelerate the development atherosclerosis in the coronary arteries. The combination of increased demand and lessened supply increases the likelihood of myocardial ischemia leading to myocardial infarction, sudden death, arrhythmias and congestive heart failure.

Ischemia is defined by an organ or a part of the body failing to receive a sufficient blood supply. An organ that is deprived of a blood supply is said to be hypoxic. An organ will become hypoxic even when the blood supply temporarily ceases, such as during a surgical procedure or during temporary artery blockage. Ischemia leads to structural and functional abnormalities, such as arrhythmias, cell death and ventricular remodeling. When the organ affected is the heart this condition is known as ischemic heart disease.

When blood flow resumes to an organ after temporary cessation, this is known as ischemic reperfusion of the organ. Ischemic reperfusion to an organ also leads to injury of the organ by producing structural and functional abnormalities in the tissue of the organ. Conditions observed with ischemia reperfusion injury include neutrophil infiltration, and necrosis.

SUMMARY OF THE INVENTION

The present invention relates to the discovery that pyridoxal-5'-phosphate (PLP and also called P-5P), described herein, can be used to treat hypertrophy, hypertension, congestive heart failure, ischemic heart disease, ischemia reperfusion injuries in an organ and to treat arrhythmia and contractile dysfunction subsequent to myocardial infarction.

Pyridoxal-5'-phosphate, PLP, is, chemically, 3-hydroxy-2-methyl-5-[(phosphonooxy)methyl]-4-pyridine-carboxaldehyde, of chemical formula:

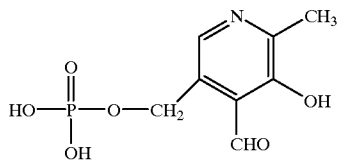

PLP can be chemically synthesized in a number of ways, for example, by the action of ATP on pyridoxal, by the action of phosphorus oxychloride on pyridoxal in aqueous solution, and by phosphorylation of pyridoxamine with concentrated phosphoric acid followed by oxidation.

The biological role of PLP is believed to include acting as a coenzyme and as an antagonist. PLP is a coenzyme at the glycogen phosphorylase level (glycogenolysis) and at the transamination level in the malate aspartate shuttle (glycolysis and glycogenolysis). To date, PLP has been therapeutically used as an enzyme cofactor vitamin.

The present invention includes methods and compositions for treating cardiovascular diseases and diseases related thereto. In one aspect, the invention includes a method for treating hypertrophy, hypertension, congestive heart failure, ischemic heart disease, ischemia reperfusion injury and cellular dysfunction in mammals that includes administering to the mammal a therapeutically effective amount of a compound selected from the group consisting of pyridoxal-5'-phosphate, pyridoxine, pyridoxal, and pyridoxamine.

In another aspect, the invention is directed to a pharmaceutical composition that includes a pharmaceutically acceptable carrier and a therapeutically effective amount, from about 0.5 to about 100 mg/kg, of a compound selected from the group consisting of pyridoxal-5'-phosphate, pyridoxine, pyridoxal, and pyridoxamine for treating hypertrophy, hypertension, congestive heart failure, ischemic heart disease, ischemia reperfusion injury and cellular dysfunction.

DESCRIPTION OF THE INVENTION

The present invention provides compositions and methods for treatment of cardiovascular and related diseases or conditions. Such cardiovascular and related diseases include hypertrophy, hypertension, congestive heart failure, ischemia reperfusion injury and cellular dysfunction. Examples of cellular dysfunction include arrhythmia and heart dysfunction subsequent to myocardial infarction.

In accordance with the present invention, it has been found that PLP can be used in the treatment of the above-identified diseases and conditions. "Treatment" and "treating" as used herein include preventing, inhibiting, and alleviating cardiovascular diseases and related symptoms as well as healing the ischemia-related conditions or symptoms thereof affecting mammalian organs and tissues. Thus a composition of the present invention can be administered in a therapeutically effective amount to a patient before, during and after any above-mentioned condition arises. As an example, for instance, a composition of the present invention can be administered prior to ischemia to prevent, inhibit, or protect against ischemia reperfusion injuries and cellular dysfunction of organs and tissues. Alternatively, a composition of the invention can be administered during or following ischemia (including during or following reperfusion) to alleviate or heal ischemia reperfusion injuries and cellular dysfunction of organs and tissues.

In one aspect, the invention is directed to a method of treating hypertrophy, hypertension, congestive heart failure, ischemic heart disease, ischemia reperfusion injury and cellular dysfunction in mammals comprising administering to the mammal a therapeutic amount of a compound selected from the group consisting of pyridoxal-5'-phosphate, pyridoxine, pyridoxal, and pyridoxamine. Cellular dysfunction may include an arrhythmia of the heart or heart failure resulting from myocardial infarction. A "therapeutic amount" as used herein includes a prophylactic amount, for example, an amount effective for preventing or protecting against ischemia-related conditions, and amounts effective for alleviating or healing ischemia-related conditions.

Administering a therapeutic amount of the compound for treating hypertrophy, hypertension, congestive heart failure, ischemic heart disease, ischemia reperfusion injury and cellular dysfunction preferably is in the range of about 0.5–100 mg/kg of a patient's body weight, more preferably in the range of about 0.5–50 mg/kg of a patient's body weight, per daily dose. The compound may be administered for periods of short and long durations depending on the condition treated.

A therapeutic amount of the compound for particularly treating ischemia-related conditions can be administered before, during, or following ischemia (including during or following reperfusion), as well as continually for some period spanning from pre- to post-ischemia. For example, the compound may be administered prior to heart procedures, including bypass surgery, thrombolysis, and angioplasty, and prior to any other procedures that require interruption and then resumption of blood flow to any organ. Additionally, the compound may be taken on a regular basis to protect against cellular dysfunction arising from arrhythmia and heart failure.

By way of illustration, the following describes administration to a human of a pharmaceutical composition containing PLP for ischemic hyperfusion. When a human is presented for a heart procedure, for example, bypass surgery, thrombolysis, or angioplasty, or for a procedure requiring interruption of blood flow to any organ, an aqueous solution comprising PLP in a therapeutic amount can be given intravenously, immediately prior to surgery and then throughout a patient's hospitalization. Alternatively, the pharmaceutical composition comprising PLP can be given immediately prior to surgery and then continuously for up to one week following surgery.

Similarly, a human may be administered an enteral dose of PLP beginning with the onset of symptoms of ischemia-related conditions through the surgical procedure. Furthermore, a human at risk for arrhythmia or heart failure may be administered a regular enteral dose of PLP to protect against cellular dysfunction.

In one aspect of the invention, a method of treating ischemia reperfusion injury and cellular dysfunction in mammals includes administering to the mammal a therapeutic amount of PLP for treating the ischemia reperfusion injury and cellular dysfunction. In another aspect, the compound administered may be pyridoxine, pyridoxal, or pyridoxamine.

In yet another aspect of the invention, a method of preventing or treating a particular cellular dysfunction known as arrhythmia of the heart in mammals includes administering to the mammal a therapeutic amount of a compound selected from the group consisting of pyridoxal-5'-phosphate, pyridoxine, pyridoxal, or pyridoxamine for treating arrhythmia of the heart. In still another aspect of the invention, the cellular dysfunction that is treated is heart failure resulting from myocardial infarction.

A pharmaceutical composition of the present invention is directed to a composition suitable for the treatment of hypertrophy, hypertension, congestive heart failure, ischemic heart disease, ischemia reperfusion injury and cellular dysfunction. The pharmaceutical composition comprises a pharmaceutically acceptable carrier and a compound selected from the group consisting of pyridoxal-5'-phosphate, pyridoxine, pyridoxal, and pyridoxamine. A pharmaceutically acceptable carrier includes, but is not limited to, physiological saline, ringers, phosphate buffered saline, and other carriers known in the art. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective. Preferably, the compound selected is PLP.

The pharmaceutical compositions may be administered enterally and parenterally. Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition should be at or near body temperature.

Methods of preparing pharmaceutical compositions containing a pharmaceutically acceptable carrier and a therapeutic compound selected from PLP, pyridoxine, pyridoxal, and pyridoxamine are known to those of skill in the art. As an illustration, a method of preparing a pharmaceutical composition containing PLP will be described.

Generally, a PLP solution may be prepared by simply mixing PLP with a pharmaceutically acceptable solution, for example, buffered aqueous saline solution at an acidic or alkaline pH (because PLP is essentially insoluble in water, alcohol, and ether), at a temperature of at least room temperature and under sterile conditions. Preferably, the PLP solution is prepared immediately prior to administration to the mammal. However, if the PLP solution is prepared at a time more than immediately prior to the administration to the mammal, the prepared solution should be stored under sterile, refrigerated conditions. Furthermore, because PLP is light sensitive, the PLP solution should be stored in containers suitable for protecting the PLP solution from the light, such as amber-colored vials or bottles.

It has been found, according to the present invention, that PLP, pyridoxine, pyridoxal, and pyridoxamine appropriately administered can have previously unexpected, highly beneficial effects in treating hypertrophy, hypertension, congestive heart failure, or ischemia reperfusion injuries in mammals and in treatment of heart dysfunction subsequent to coronary occlusion. For illustrative purposes, the beneficial effect of administering PLP is demonstrated in the specific examples detailed below. The Examples describe both in vitro and in vivo experiments.

DESCRIPTION OF CLINICAL EXPERIMENTS

Example I

In Vitro-Ischemia Reperfusion in Isolated Rat Hearts and Measurement of Left Ventricular Developed Pressure Male Sprague-Dawley rats (200–250 g) were sacrificed by decapitation, and their hearts were rapidly removed and perfused according to the Langendorff procedure at a constant flow of 10 ml/min using the Kreb's-Heinsleit buffer (K-H buffer) oxygenated with 95% $O_2$ and 5% $CO_2$, pH 7.4. After equilibration, a Langendorff Perfusion apparatus using K-H buffer was used to study the effect of PLP on ischemia reperfusion.

After an equilibration period of 15 min, total ischemia was induced by stopping the perfusion for 30 min while the hearts were kept at constant humidity and temperature of 37° C. In ischemic-reperfused hearts, perfusion with normal K-H buffer was reinstated for 60 min after 30 min of global ischemia. The hearts were electrically stimulated (Phipps and Bird stimulator) at 300 beats/min via a square wave of 1.5 ms duration at twice the threshold voltage. The left ventricular developed pressure (LVDP), the rate of change in developed pressure (+dP/dt) and the rate of change in relaxation (−dP/dt) were measured by using a water filled latex balloon inserted into the left ventricle. The volume of the balloon as adjusted at the left ventricular end-diastolic pressure (LVEDP) of 10 mm Hg at the beginning of each experiment, and the balloon was connected to pressure transducer (model 1050BP-BIOPAC SYSTEMS INC.). Data was recorded on-line through analogue-digital interface (MP 100, BIOPAC SYSTEMS INC.) and stored and processed with "Acknowledge 3.01 for Windows" (BIOPAC SYSTEM INC.). In experiments where the effect of the pyridoxal-5'-phosphate (PLP) were studied, the hearts were perfused with PLP (15 $\mu$M)+K-H buffer for 10 min before inducing ischemia. This delivery of PLP (15 $\mu$M) in the K-H buffer was continued throughout the reperfusion period in these experiments.

The left ventricular developed pressure (LVDP) reflects the contractile activity of the heart.

Once the heart was reperfused after ischemia, it tends to become arrhythmic. There is a time lapse before the heart stabilizes into a normal mode of rhythm.

The results of these experiments are shown below in Table 1. The control group comprised 13 animals, the PLP-treated group comprised 6 animals. All values in the Table are percentage of pre-ischemic values.

Global ischemia resulted in a decline of left ventricular developed pressure (LVDP). Reperfusion of the ischemic heart was found to induce a slow recovery of changes in LVDP. These parameters showed about 40% recovery over a 60 min reperfusion period.

On the other hand, about 80% recovery of depressions in LVDP was evident upon reperfusion of the hearts with PLP 10 min before inducing ischemia. Also the time to 50% recovery (time taken to reach half of the maximum contractile force recovery on reperfusion) was reduced in treated hearts.

TABLE 1

| Parameters | Control | Treated |
| --- | --- | --- |
| Time to regular rhythm (min) | 18.3 ± 5.0 | 5.3 ± 2.1 |
| LVDP - 30 min (% recovery) | 30 ± 8.6 | 78.2 ± 9.2 |
| LVDP - 60 min (% recovery) | 44.2 ± 9.3 | 84.7 ± 6.3 |
| Time to 50% recovery (Min) | 39.3 ± 8.1 | 16.0 ± 4.6 |

Example 2

In Vitro-Isolation of Membrane Preparation and Determination of Adenylyl Cyclase Activity At the end of each perfusion/reperfusion period, the heart was removed from the cannula and the crude membranes were prepared by the method used previously by Sethi et al., *J. Cardiac Failure*, 1(5) (1995) and Sethi et al., *Am. J. Physiol.*, 272 (1997). Briefly, the hearts were minced and then homogenized in 50 mM Tris-HCl, pH 7.5 (15 ml/g tissue) with a PT-20 polytron (Brinkman Instruments, Westbury, N.Y., USA), twice for 20s each at a setting of 5. The resulting homogenate was centrifuged at 1000×g for 10 min and the pellet was discarded. The supernatant was centrifuged at 3048000×g for 25 min. The resulting pellet was resuspended and centrifuged twice in the same buffer and at the same speed; the final pellet was resuspended in 50 mM Tris-HCl, pH 7.4 and used for various biochemical assays.

Adenylyl cyclase activity is increased during ischemia reperfusion leading to arrhythmias and damage to the myocardium due to increased cAMP levels and increased calcium entry. Treatment with PLP partially reverses this increased enzyme activity to control levels.

The adenylyl cyclase activity was determined by measuring the formation of [$\alpha$-$^{32}$P] cAMP [$\alpha$-$^{32}$P] ATP as described by Sethi et al., supra. Unless otherwise indicated, the incubation assay medium contained 50 mM glycylglycine (pH 7.5), 0.5 mM Mg ATP, [[$\alpha$-$^{32}$P] ATP (1–1.5×106 cpm), 5 mM $MgCl_2$ (in excess of the ATP concentration), 100 mM NaCl, 0.5 mM cAMP, 0.1 mM EGTA, 0.5 mM 3-isobutyl-1-methylxanthine, 10 U/ml adenosine deaminase, and an ATP regenerating system comprising of 2 mM creatine phosphate and 0.1 mg creatine kinase/ml in a final volume of 200 $\mu$l. Incubations were initiated by the addition of membrane (30–70 ug) to the reaction mixture, which had equilibrated for 3 min at 37° C. The incubation time was 10 min at 37° C. and the reaction was terminated by the addition of 0.6 ml 120 mM zinc acetate containing 0.5 mM unlabelled cAMP. The [$\alpha$-$^{32}$P] cAMP formed during the reaction was determined upon coprecipitation of other nucleotides with $NaCO_3$ by the addition of 0.5 ml 144 mM $Na_2CO_3$ and subsequent chromatography. The unlabelled cAMP served to monitor the recovery of [$\alpha$-$^{32}$P] cAMP by measuring absorbency at 259 nm. Under the assay conditions used, the adenylyl cyclase activity was linear with respect to protein concentration and time of incubation.

In a control Group C, the membrane preparation prepared as described in Example 2 was from hearts which, after a 20 minute stabilizing period, were perfused with normal K-H buffer or normal K-H buffer plus PLP for 90 minutes. In a group denoted IR (ischemia reperfusion), the membrane preparation was from hearts in which, after a 20 minute stabilizing period, ischemia was induced for 30 minutes followed by 60 minutes reperfusion with normal K-H buffer. In a group denoted PR, the preparation was from hearts in which, after a 20 minute stabilizing period, the hearts were perfused with 15 $\mu$m PLP plus normal K-H buffer for 10 minutes, followed by ischemia induced for 30 minutes followed by 60 minutes reperfusion with normal K-H buffer. Note that PLP was present all through the reperfusion period.

The results are shown in Table 2. They are from n=6 experiments.

TABLE 2

Effect of various stimulants on adenylyl cyclase activity
in rat heart crude membrane preparations from control (C),
ischemia reperfusion (IR), and treated group (PR).
Adenyl Cyclase Activity pmol cAMP/mg protein/10 min

| Group | Basal | NaF (5 mM) | Forskolin (100 μM) | Gpp(NH)p (30 μM) |
|---|---|---|---|---|
| Control | 296 ± 32 | 2343 ± 118 | 1423 ± 102 | 1123 ± 98 |
| IR | 529 ± 21* | 3490 ± 176* | 2192 ± 111* | 1865 ± 81* |
| PR | 391 ± 18# | 2960 ± 132# | 1804 ± 129# | 1492 ± 101# |

*P < 0.05, significantly different from Control and PR group.
P < 0.05, significantly different from Control and IR group.

Example 3

In Vivo-Coronary Artery Ligation

Myocardial infarction was produced in male Sprague-Dawley rats (200–250 g) by occlusion of the left coronary artery as described by Sethi et al., supra. Rats were anesthetized with 1–5% isoflurane in 100% 02 (2 L flow rate). The skin was incised along the left sterna border and the 4th rib was cut proximal to the sternum and a retractor inserted. The pericardial sac was opened and the heart externalized. The left anterior descending coronary artery was ligated approximately 2 mm from its origin on the aorta using a 6-0 silk suture. The heart was then repositioned in the chest and the incision closed via purse-string sutures. Sham operated rats underwent identical treatment except that the artery was not ligated. Mortality due to surgery was less than 1%. Unless indicated in the text, the experimental animals showing infarct size >30% of the left ventricle were used in this study. All animals were allowed to recover, received food and water ad libitum, and were maintained for a period of 21 days for Electrocardiogram (ECG), hemodynamic and histological assessment.

Occlusion of the coronary artery in rats has been shown to produce myocardial cell damage which results in scar formation in the left ventricle and heart dysfunction. While the complete healing of the scar occurs within 3 weeks of the coronary occlusion, mild, moderate and severe stages of congestive heart failure have been reported to occur at 4, 8 and 16 weeks after ligation. Accordingly, the contractile dysfunction seen at 3 weeks after the coronary occlusion in rats is due to acute ischemic changes.

The rats were housed in clear cages in a temperature and humidity controlled room, on a 12 hour light-dark cycle. Food and water were supplied ad libitum. Rats at random were divided into five groups: sham operated, coronary artery ligated without treatment, sham operated with PLP treatment, coronary artery ligated with PLP treatment (25 mg/kg body weight orally by gastric gauge) two days before surgery, and coronary artery ligated with PLP treatment (25 mg/kg body weight) one hour after surgery. These animals were used in all the studies below. For EKG studies, these animals were used as their controls before surgery, so that before surgery was done on these animals EKG traces were taken which were then used as controls for the same animals after surgery.

Example 4

In Vivo-Hemodynamic Changes

The animals prepared as described in Example 3 were anesthetized with an injection of cocktail of ketamine hydrochloride (60 mg/kg) and xylazine (10 mg/kg). The right carotid artery was exposed, and cannulated with a microtip pressure transducer (model PR-249, Millar Instruments, Houston, Tex.). The catheter was advanced carefully through the lumen of the carotid artery until the tip of the transducer entered the left ventricle. The catheter was secured with a silk ligature around the artery. The hemodynamic parameters such as left ventricular systolic pressure (LVLSP), left ventricular end diastolic pressure (LVEDP), rate of contraction (+dP/dt), and rate of relaxation (−dP/dt) were recorded on a computer system (AcqKnowledge 3.1 Harvard, Montreal, Canada).

Myocardial infarction for 3 weeks produced a progressive increase in left ventricular end diastolic pressure (LVEDP) without any changes in either heart rate of left ventricular systolic pressure (LVSP). Furthermore, both rate of force of contraction (+dP/dt) and rate of force of relaxation (−dP/dt) were significantly depressed in the infarcted animals. The elevation in LVEDP and depression in both +dP/dt and −dP/dt were partially prevented upon treating the infarcted animals with PLP for 3 weeks.

The results are given below, in Tables 3 and 4.

Data are expressed as mean±SE of 10 animals. All measurements were made using a Miller microcatheter; the catheter was inserted into the left ventricle via cannulation of the right carotid artery. LVSP, left ventricular systolic pressure; LVEDP, left ventricular end-diastolic pressure; +dP/dt, rate of contraction; −dP/dt rate of relaxation. Animals were randomly divided into four groups. Sham, Sham+ Drug treated, Drug treated starting at 2 days before ligation (PrD) for up to 21 days and coronary ligated group (Ml). Treatment group was given PLP (25 mg/kg body wt.) orally by gastric gauge once a day.

TABLE 3

Hemodynamic parameters of rates with myocardial
infarction with or without PLP treatment for 21 days
starting at 2 days before coronary artery ligation (PrD).

| Parameters | Sham | Sham + Drug | MI | PrD |
|---|---|---|---|---|
| HR (beats/min) | 376 ± 18 | 398 ± 22 | 405 ± 22 | 475 ± 16 |
| LVSP (mm Hg) | 126 ± 7 | 122 ± 6 | 128 ± 6 | 123 ± 6 |
| LVEDP (mm Hg) | 2.2 ± 0.2 | 1.9 ± 0.09 | 12.2 ± 0.9* | 5.7 ± 0.9# |
| +dP/dt (mm Hg/s) | 5899 ± 302 | 5772 ± 312 | 2654 ± 111* | 4272 ± 223# |
| −dP/dt (mm Hg/s) | 5469 ± 284 | 5401 ± 297 | 2348 ± 99* | 3998 ± 179# |

*(P < 0.05) significantly different from the sham control and the PrD group.
(P < 0.05) significantly different from sham control group and MI group.

TABLE 4

A later confirmation of hemodynamic parameters of
rates with myocardial infarction with or without PLP
treatment for 21 days starting at 1 hour after and
2 days before coronary artery ligation.

| Parameters | Sham | Sham + Drug | MI | PP1 | PP2 |
|---|---|---|---|---|---|
| HR (beats/min) | 381 ± 18 | 396 ± 22 | 402 ± 22 | 378 ± 16 | 381 ± 10 |
| LVSP (mm Hg) | 124 ± 7 | 122 ± 6 | 124 ± 6 | 127 ± 6 | 129 ± 5 |

TABLE 4-continued

A later confirmation of hemodynamic parameters of
rates with myocardial infarction with or without PLP
treatment for 21 days starting at 1 hour after and
2 days before coronary artery ligation.

| Parameters | Sham | Sham + Drug | MI | PP1 | PP2 |
|---|---|---|---|---|---|
| LVEDP (mm Hg) | 2.2 ± 0.2 | 1.9 ± 0.09 | 12.2 ± 0.9* | 5.7 ± 0.9*# | 5.2 ± 0.8*# |
| +dP/dt (mm Hg/s) | 5899 ± 302 | 5772 ± 312 | 2654 ± 111* | 4272 ± 223*# | 4199 ± 219*# |
| −dP/dt (mm Hg/s) | 5469 ± 284 | 5401 ± 297 | 2348 ± 99* | 3998 ± 179*# | 3918 ± 177*# |

*($p < 0.05$) significantly different from the sham and sham + drug group.
($p < 0.05$) significantly different from MI group.

There were three groups of rats, 20 each: (MI) untreated coronary litigated, (PP1) orally PLP once daily starting at 1 hour after ligation, (PP2) orally PLP once daily starting at 2 days before ligation.

Example 5

In Vivo-Electrocardiogram (ECG) Recordings

Six lead (I, II, III, aVr, aVf, aVl) ECG recordings were made from rats in all groups (sham operated, coronary artery ligated (MI), sham operated with drug treatment, coronary artery ligated with drug treatment 2 days before ligation, coronary artery ligation with drug treatment within 1 hour of ligation) prior to coronary artery ligation and at 1, 3, 7, 14 and 21 days after occlusion. Surface ECG's were recorded under isoflurane anesthesia using a model EC-60 Cardiac and Respiratory monitor (Silogic International Limited, U.K.). The ST segment abnormality was defined as depression or elevation of at least 1 mm from the base line that persisted for $\geq 1$ min. The magnitude of the ST segment shift was measured 60 ms after the J point in all of the six leads. The QT interval was measured by standard criteria and then corrected for heart rate using Bazett's formula ($QT_c = QT/$ square root of RR interval). The longest QT interval of all lead was measured from onset of the Q-wave until termination of the T wave. Onset of the R wave was used if Q waves were not present. The R—R interval immediately preceding the QT interval measurement was used to correct for heart rate. Pathological Q-waves were defined as a negative deflection, at least 25 uV in amplitude, preceding the R-wave.

ST Segment Changes

ST-segment depression reflecting subendocardial hypoperfusion is the most common ECG manifestation of ischemia, and ST segment deviation can be used as a noninvasive marker of the perfusion status of the heart. Electrodes positioned directly over the injured zone typically record ST segment elevation whereas those in opposite areas of the torso detect "reciprocal" ST segment depression. In the present study, ST segment depression was recorded in lead I and ST segment elevation in leads II and III three leads at 1 to 21 days after coronary artery ligation in untreated rats. Treatment with PLP attenuated the degree of ST segment elevation/depression following occlusion, and accelerated recovery of the ST segment. The results are shown below in Tables 5 and 6. In Table 5, the values for ST segment deviation recorded prior to the occlusion (control) for all the three leads for MI and PrD group were 0.01, 0.02, 0.01 and 0.01 5, 0.02 and 0.01 respectively. In Table 6, the values for ST segment deviation recorded prior to the occlusion (control) for all the three leads for MI and PrD group were 0.02, 0.02, 0.01 and 0.01, 0.009 and 0.015 respectively.

TABLE 5

ST segment changes in rats with myocardial infarction
(MI) with or without PLP treatment for 21 days starting
at 2 days before coronary artery ligation (PrD).
ST segment (mV)

| Group | 7 Day | 14 Day | 21 Day |
|---|---|---|---|
| Lead I | | | |
| MI | 0.17 ± 0.02* | 0.17 ± 0.02* | 0.15 ± 0.01* |
| PrD | 0.08 ± 0.01 | 0.05 ± 0.01 | 0.03 ± 0.01 |
| Lead II | | | |
| MI | 0.15 ± 0.01* | 0.15 ± 0.01* | 0.14 ± 0.01* |
| PrD | 0.07 ± 0.01 | 0.04 ± 0.01 | 0.03 ± 0.01 |
| Lead III | | | |
| MI | 0.18 ± 0.02* | 0.17 ± 0.02* | 0.14 ± 0.01* |
| PrD | 0.06 ± 0.01 | 0.04 ± 0.01 | 0.02 ± 0.01 |

*$P < 0.05$ compared to control and treated group.

TABLE 6

ST segment changes in rats with myocardial
infarction (MI with or without PLP treatment for 7 days
starting at 1 hour after coronary artery ligation (PrD).
ST segment (mV)

| Group | 1 Day | 3 Day | 7 Day |
|---|---|---|---|
| Lead I | | | |
| MI | 0.19 ± 0.02* | 0.19 ± 0.02* | 0.16 ± 0.01* |
| PrD | 0.13 ± 0.01 | 0.09 ± 0.01 | 0.07 ± 0.01 |
| Lead II | | | |
| MI | 0.20 ± 0.01* | 0.19 ± 0.01* | 0.17 ± 0.01* |
| PrD | 0.14 ± 0.01 | 0.10 ± 0.01 | 0.07 ± 0.01 |
| Lead III | | | |
| MI | 0.20 ± 0.02* | 0.18 ± 0.01* | 0.15 ± 0.01* |
| PrD | 0.13 ± 0.01 | 0.08 ± 0.01 | 0.04 ± 0.01 |

* $P < 0.05$ compared to control and treated group.

QT Interval and Mortality Following Myocardial Infarction

The QT interval on the surface electrocardiogram is an indirect measure of the ventricular action potential duration and its prolongation is often associated with the occurrence of malignant ventricular arrhythmias in patients. A long QT interval on the ECG is associated with a higher risk of sudden cardiac death following myocardial infarction. The data indicates that QT interval prolongation occurred by 1 day and then gradually declined from 3–21 days which coincided with the period of highest mortality following ligation in untreated rats. Treatment with PLP attenuated the QT prolongation and also accelerated the time course of recovery of the QT interval following coronary occlusion.

The results are given below in Tables 7, 8 and 9.

Myocardial infarction was induced by coronary ligation. All the animals remaining after subsequent weeks were used for ECG estimations. Values are mean±SE. Treated animals were given PLP (25 mg/kg) orally once or twice a day. Control values were taken before the induction of myocardial infarction.

TABLE 7

Time dependent changes of $QT_c$ interval (msec) in myocardial infarction with or without PLP treatment for up to 21 days starting at 2 days before coronary artery ligation (PrD).

| Group | Control | 7 Day | 14 Day | 21 Day |
|---|---|---|---|---|
| MI | 302 ± 17 | 563 ± 32* | 522 ± 26* | 506 ± 29* |
| PrD | 313 ± 21 | 456 ± 22*# | 437 ± 23*# | 410 ± 21*# |

*P < 0.05 compared to control.
P < 0.05 compared with MI group.

There were two groups of rats, 20 each: (MI) untreated coronary litigated, (PrD) PLP orally once daily.

TABLE 8

Later confirmation and expansion of time dependent changes of $QT_c$ interval (msec) in myocardial infarction with or without PLP treatment for up to 21 days starting at 2 days before coronary artery ligation.

| Group | Control | 1 Day | 3 Day | 7 Day | 21 Day |
|---|---|---|---|---|---|
| MI | 302 ± 17 | 601 ± 17* | 571 ± 18* | 522 ± 26* | 506 ± 29* |
| PP1 | 313 ± 23 | 530 ± 25*# | 486 ± 15*# | 457 ± 23*# | 410 ± 21# |
| PP2 | 316 ± 24 | 541 ± 33*# | 495 ± 31*# | 452 ± 19*# | 401 ± 17* |

*P < 0.005 compared to control.
P < 0.005 compared with MI group.

There were three groups of rats, 20 each: (MI) untreated coronary litigated, (PP1) orally PLP once daily, (PP2) orally PLP twice daily. n=20, values mean±SE. Control values taken before induction of myocardial infarction.

TABLE 9

Time dependent changes of $QT_c$ interval (msec) in myocardial infarction with or without PLP treatment for up to 21 days starting at 1 hour after coronary artery ligation.

| Group | Control | 1 Day | 3 Day | 7 Day | 21 Day |
|---|---|---|---|---|---|
| MI | 322 ± 17 | 594 ± 22* | 562 ± 18* | 540 ± 20* | 503 ± 22* |
| PP1 | 310 ± 21 | 516 ± 21*# | 505 ± 13*# | 430 ± 11*# | 404 ± 18*# |
| PP2 | 311 ± 14 | 535 ± 23*# | 484 ± 21–# | 421 ± 26*# | 397 ± 19*# |

*P < 0.05 compared to control.
P < 0.05 compared with MI group.

There were three groups of rats, 20 each: (MI) untreated coronary litigated, (PP1) orally PLP once daily, (PP2) orally PLP twice daily. n=20, values are mean±SE. Control values were taken before induction of myocardial infarction.

Accordingly the mortality rate was also significantly less in the PLP treated group.

Mortality Rates

Most early deaths after myocardial infarction occur within the first few hours and these are caused primarily by lethal ventricular arrhythmias. In the present study, mortality was highest in the first 48 hours after coronary ligation in both untreated and treated rats, however, mortality was significantly less in treated animals. This decreased mortality was accompanied by several improved ECG findings suggesting an antiarrhythmic action of PLP (decreased incidences of pathological Q-waves and PVCS).

Rats intended for operating on, were randomly divided into four groups, each 20: Sham, Sham+Drug treated, Drug treated starting at 2 days before ligation (MI+Drug) for up to 21 days and Coronary ligated (MI). Since the sham and sham+drug group had no differences in regards to mortality and other hemodynamic changes, they were considered as one group. The results are shown below in Tables 10, 11, 12 and 13.

TABLE 10

Mortality in rats with myocardial infarction with or without PLP treatment for 21 days starting at 2 days before coronary artery ligation (PrD).

| | No. of animals (%) | |
|---|---|---|
| Mortality | MI | PrD |
| On the 1st day | 30 | 15 |
| On the 2nd day | 10 | 5 |
| On the 3rd day | 5 | 0 |
| Within 21 days (%) ## | 45 | 20* |

*Significantly (P < 0.05) different from the MI group. Sham group had no mortality.

At the 21st day, 3 animals from the MI group appeared very sick and may not have survived another week.

TABLE 11

Later confirmation and expansion of mortality in rats with myocardial infarction with or without PLP treatment for 21 days starting at 2 days before coronary artery ligation.

| | No. of animals (%) | | |
|---|---|---|---|
| Mortality | MI | PP1 | PP2 |
| On the 1st day | 30 | 20 | 20 |
| On the 2nd day | 10 | 5 | 5 |
| On the 3rd day | 5 | 0 | 5 |
| Within 21 days (%) | 45 | 25* | 30* |

*Significantly (P < 0.05) different from the MI group.

(MI) untreated coronary litigated, (PP1) orally PLP once daily, (PP2) orally PLP twice daily.

In a second, similar test, rats intended for operating on, were randomly divided into four groups, 20 each: Sham, Sham+Drug treated, drug treated starting at 1 hour after ligation (PrD) for up to 7 days and coronary ligated group (MI). Since the sham and sham+drug group had no differences in regards to mortality and other hemodynamic changes, they were considered as one group.

The results are shown below in Table 12.

TABLE 12

Mortality in rats with myocardial infarction with or without PLP treatment for 7 days starting at 1 hour after coronary artery ligation (PrD).

| | No. of animals (%) | |
|---|---|---|
| Mortality | MI | PrD |
| On the 1st day | 25 | 15 |
| On the 2nd day | 15 | 5 |
| On the 3rd day | 5 | 0 |
| Within 7 days (%) | 45 | 20* |

*Significantly (P < 0.05) different from the MI group. Sham group had no mortality.

TABLE 13

Later confirmation and expansion of mortality in rats
with myocardial infarction with or without PLP treatment
for 21 days starting at 1 hour after coronary artery ligation.

| | No. of animals (%) | | |
|---|---|---|---|
| Mortality | MI | PP1 | PP2 |
| On the 1st day | 30 | 20 | 16 |
| On the 2nd day | 10 | 8 | 8 |
| On the 3rd day | 5 | 0 | 0 |
| Within 21 days (%) | 45 | 28* | 24* |

*Significantly ($P < 0.05$) different from the MI group.

There were three groups of rats: (MI), 20 rats, untreated coronary litigated, (PP1), 25 rats, orally PLP once daily, (PP2), 25 rats, orally PLP twice daily.

Antiarrhythmic Action of PLP Revealed by ECG's

The ECGs of the animals in the previously reported tests for mortality rate showed several findings indicating an antiarrythmic action of PLP. One of these is a decreased incidence of pathological Q-waves.

These results are shown in Tables 14 and 15 below.

TABLE 14

General Characteristics and pathological "Q" wave appearance of
rats with myocardial infarction with or without PLP treatment for
up to 21 days, starting at 1 hour after coronary artery ligation.

| Parameters | Sham | Sham + Drug | MI | PP1 | PP2 |
|---|---|---|---|---|---|
| Body wt. (g) | 321 ± 3 | 312 ± 4 | 332 ± 5 | 342 ± 7 | 344 ± 10 |
| Q wave appearance within 21 days (%) (Pathological) | — | — | 58 | 27* | 38* |
| Infarct size (% of LV) | — | — | 43 | 21* | 23* |

*Significantly ($P < 0.05$) different from the MI group.

There were three groups of rats, 20 each: (MI) untreated coronary litigated, (PP1) orally PLP once daily, (PP2) orally PLP twice daily. n=20, values are mean±SE. Sham group was given saline.

TABLE 15

General Characteristics and pathological "Q" wave appearance
of rats with myocardial infarction with or without PLP treatment
for up to 21 days, 2 days after coronary artery ligation.

| Parameters | Sham | Sham + Drug | MI | PP1 | PP2 |
|---|---|---|---|---|---|
| Body wt. (g) | 330 ± 8 | 322 ± 5 | 331 ± 7 | 332 ± 9 | 334 ± 10 |
| Q wave appearance within 21 days (%) (Pathological) | — | — | 62 | 37* | 39* |
| Infarct size (% of LV) | — | — | 43 | 27* | 32* |

*Significantly ($P < 0.05$) different from the MI group.

There were three groups of rats, 20 each: (MI) untreated coronary litigated, (PP1) injected PLP once daily, (PP2) injected PLP twice daily. n=20, values are mean±SE. Sham group was given saline.

Another such finding is a decreased incidence of preventricular contraction (PVC) following coronary artery ligation. These results are shown in Tables 16 and 17 below.

TABLE 16

Effect of treatment with PLP (starting at 2 days before ligation
continued for 21 days) on the incidence of preventricular
contraction (PVC) following coronary artery ligation.

| | PVC Incidence (%) | | |
|---|---|---|---|
| Group | 7 Day | 14 Day | 21 Day |
| MI | 23 | 23 | 18 |
| PrD | 2* | 3* | 3* |

*Significantly ($P < 0.05$) different from the MI group.

TABLE 17

Effect of treatment with PLP (starting at 1 hour after ligation
continued for 7 days) on the incidence of preventricular contraction
(PVC) following coronary artery ligation.

| | PVC Incidence (%) | | |
|---|---|---|---|
| Group | 1 Day | 3 Day | 7 Day |
| MI | 14 | 14 | 21 |
| PrD | 1* | 1* | 3* |

*Significantly ($P < 0.05$) different from the MI group.

Example 6

In Vivo-Congestive Heart Failure

It has been demonstrated by Sethi et al., Am. J. Physiol., supra, (see Example 3) and J. Mol. Cell. Cardiol. 30; 2153–2163, 1999, that the rat model of congestive heart failure after 4, 8 and 16 weeks of ligation is classified as early, moderate and severe stages of congestive heart failure respectively due to the occurrence of ascites. In this model of congestive heart failure the descending coronary artery of the rat heart is ligated. The chest is then closed and the animals are kept alive for 16 weeks during which you see a progression from heart failure to congestive heart failure. Since congestion is one of the markers that differentiate heart failure from congestive heart failure, we have studied ascites (accumulation of fluid in the abdomen) a marker for congestion. Ascites is also evident in other models of congestive heart failure such as the cardiomyopathic hamster. However, at 2–3 weeks of ligation, the stage is referred to as ischemia stage of heart failure since at that point no congestion is observed. Pervious studies by other investigators have also shown similar time dependent classification in this model. Afzal et al., *Am. J. Physiol,* 262(31); H868–874, 1992, and Dixon et al., Coron. Artery Dis. 2; 805–814, 1991. In our model the accumulation of fluid in the abdomen is significantly more in untreated animals. The treated group demonstrated a significantly less amount of fluid in the abdomen when compared to the untreated group.

Thus during congestive heart failure, in addition to a decrease in contractile parameters such as rate of force of contraction (+dP/dt) and rate of force of relaxation (−dP/dt), a significant increase with respect to fluid accumulation in the abdomen area is seen in the untreated group, Table 18. These changes are improved in treated group.

Example 7

In Vivo-Hypertrophy

Hypertrophy is a physiological condition of enlargement (increased muscle mass) of the organ due to some increased stress to that organ. One of the markers to assess cardiac hypertrophy is heart to body ratio. Table 19 shows that rats in the 8 week, sucrose induced hypertension study demonstrated a significantly increased heart to body weight index relative to the control and P-5-P treated groups. Table 18, the congestive heart failure mode, shows a similar trend between untreated and treated groups demonstrating that P-5-P has an ability to reduce hypertrophy.

Example 8

In Vivo-Hypertension

It has been well demonstrated by various investigators that feeding 8–10% sucrose in water induces hypertension in rats. Zein et al., Am. Coll. Nutr., 17 (1), 36–37, 1998; Hulman et al., Pediatr. Res., 36:95–101; Reaven et al., Am. J. Hypertens; 1991:610–614. In applying this model, we have demonstrated that treatment with P-5-P significantly decreases the sucrose-induced increase in systolic blood pressure (SBP). The blood pressure is monitored using the tail cuff method. The calculations were done using the Acknowledge™ computer software program.

TABLE 18

General characteristics (markers of hypertrophy and congestion) and hemodynamic parameters (markers of contractility) in control, untreated and treated animals in the 16 week congestive heart failure model.

| Parameters | Control | Untreated | Treated |
| --- | --- | --- | --- |
| LV wt (mg)/Body wt (g) | 1.77 ± 0.2 | 2.97 ± 0.3* | 2.22 ± 0.3 |
| Ascites (ml) | 0.7 ± 0.1 | 13.7 ± 0.3* | 6.2 ± 0.5 |
| LVEDP (% of control) | 7.9 ± 0.7 | 29.3 ± 2.7* | 17.7 ± 2.1 |
| +dP/dt (mmHg/s) | 8747 ± 439 | 6366 ± 447* | 7864 ± 483 |
| −dP/dt (mmHg/s) | 9041 ± 1383 | 7616 ± 113* | 8845 ± 539 |

Each value is a mean±SE of 6 experiments. *$P<0.05$, significantly different from control and treated group. Treated group was given 25 mg/kg orally two times a day for 16 weeks.

TABLE 19

Effect of Pyridoxal-5-phosphate (25 mg/kg) treatment on heart/body ratio (marker of hypertrophy) and systolic blood pressure (marker of hypertension) in 10% sucrose induced hypertension in rats.

| Group | Heart/body wt index (mg/100 g) | Systolic Blood Pressure mm (Hg) | |
| --- | --- | --- | --- |
| | | 0 day | 4 weeks |
| Control | 215 ± 0.04 | 121.8 ± 2.5 | 124.6 ± 3.2 |
| Sucrose (untreated) | 263 ± 0.05* | 119.8 ± 5.3 | 152.2 ± 6.2* |
| Treated | 233 ± 0.04 | 121.0 ± 3.9 | 132.8 ± 4.2 |

Each value is a mean±SE of 5 experiments. $P<0.05$-significantly different than control and treated group. Treated group is the treatment with P-5-P for 4 weeks along with sucrose. Heart to body weight index was calculated after 8 weeks of sucrose feeding in all groups.

As those skilled in the art would realize these preferred described details and compounds and methods can be subjected to substantial variation, modification, change, alteration, and substitution without affecting or modifying the function of the described embodiments.

Although embodiments of the invention have been described above, it is not limited thereto, and it will be apparent to persons skilled in the art that numerous modifications and variations form part of the present invention insofar as they do not depart from the spirit, nature and scope of the claimed and described invention.

It must be noted that, as used in this specification and the appended claims, the singular forms "a," "an," and "the" include plural referents unless the content clearly dictates otherwise. Thus, for example, reference to a composition containing "a compound" includes a mixture of two or more compounds.

We claim:

1. A method of treating hypertrophy, congestive heart failure, ischemia reperfusion injury, or arrhythmia in a mammal suffering therefrom comprising: administering to said mammal a therapeutic amount of a compound selected from the group consisting of pyridoxine, pyridoxal-5'-phosphate, pyridoxal, and pyridoxamine.

2. The method of claim 1, wherein said therapeutic amount is in a range of about 0.5–100 mg/kg per day of the mammal's body weight.

3. The method of claim 1, wherein said therapeutic amount is in a range of about 0.5–50 mg/kg per day of the mammal's body weight.

4. The method of claim 1, wherein said compound is administered enterally or parenterally.

5. The method of claim 1, wherein said compound is pyridoxal.

6. The method of claim 1, wherein said compound is pyridoxamine.

7. The method of claim 1, wherein said compound is pyridoxal-5'-phosphate.

8. A method of treating ischemia reperfusion injury in a mammal suffering therefrom comprising: administering to said mammal a therapeutic amount of a compound selected from the group consisting of pyridoxal-5'-phosphate, pyridoxine, pyridoxal, and pyridoxamine.

9. The method of claim 8, wherein said therapeutic amount is in a range of about 0.5–100 mg/kg per day of the mammal's body weight.

10. The method of claim 8, wherein said compound is pyridoxal-5'-phosphate.

11. A method of treating arrhythmia in a mammal suffering therefrom comprising: administering to said mammal a therapeutic amount of a compound selected from the group consisting of pyridoxal-5'-phosphate, pyridoxine, pyridoxal, and pyridoxamine.

12. The method of claim 11, wherein said therapeutic amount is in a range of about 0.5–100 mg/kg per day of the mammal's body weight.

13. The method of claim 11, wherein said compound is pyridoxal-5'-phosphate.

14. A method of treating hypertrophy in a mammal suffering therefrom comprising:
administering to said mammal a therapeutic amount of a compound selected from the group consisting of pyridoxal-5'-phosphate, pyridoxine, pyridoxal, and pyridoxamine.

15. The method of claim 14, wherein said therapeutic amount is in a range of about 0.5–100 mg/kg per day of the mammal's body weight.

16. The method of claim 14, wherein said compound is pyridoxal-5'-phosphate.

17. A method of treating hypertension in a mammal suffering therefrom comprising:
administering to said mammal a therapeutic amount of pyridoxal-5'-phosphate.

18. The method of claim 17, wherein said therapeutic amount is in a range of about 0.5–100 mg/kg per day of the mammal's body weight.

19. A method of treating congestive heart failure in a mammal suffering therefrom comprising:

administering to said mammal a therapeutic amount of a compound selected from the group consisting of pyridoxal-5'-phosphate, pyridoxine, pyridoxal, and pyridoxamine.

20. The method of claim 19, wherein said therapeutic amount is in a range of about 0.5–100 mg/kg of the mammal's body weight.

21. The method of claim 19, wherein said compound is pyridoxal-5'-phosphate.

22. A method of treating contractile dysfunction subsequent to myocardial infarction in a mammal suffering therefrom comprising: administering to said mammal a therapeutic amount of a compound selected from the group consisting of pyridoxal-5'-phosphate, pyridoxine, pyridoxal, and pyridoxamine.

23. The method of claim 22, wherein said therapeutic amount is in a range of about 0.5–100 mg/kg per day of the mammal's body weight.

24. The method of claim 22, wherein said compound is pyridoxal-5'-phosphate.

25. The method of claim 8, wherein said compound is administered prior to a heart procedure selected from the group consisting of bypass surgery, thrombolysis, and angioplasty.

* * * * *